United States Patent
Delbeke et al.

(10) Patent No.: US 11,992,310 B2
(45) Date of Patent: May 28, 2024

(54) PERSONAL HEALTH MONITORING SYSTEM, MULTIPLE USER HEALTH MONITORING SYSTEM, AND METHOD

(71) Applicant: Indigo Diabetes N.V., Zwijnaarde (BE)

(72) Inventors: Danaë Delbeke, Gentbrugge (BE); Koenraad Van Schuylenbergh, Vorselaar (BE); Wim Pollet, Bellingen (BE); Juan Sebastian Ordonez Orellana, Ghent (BE); Rutger Nijlunsing, Veldhoven (NL)

(73) Assignee: Indigo Diabetes N.V., Zwijnaarde (BE)

( * ) Notice: Subject to any disclaimer, the term of this patent is extended or adjusted under 35 U.S.C. 154(b) by 0 days.

(21) Appl. No.: 16/639,768

(22) PCT Filed: Aug. 17, 2018

(86) PCT No.: PCT/EP2018/072317
§ 371 (c)(1),
(2) Date: Feb. 18, 2020

(87) PCT Pub. No.: WO2019/034773
PCT Pub. Date: Feb. 21, 2019

(65) Prior Publication Data
US 2020/0205703 A1 Jul. 2, 2020

(30) Foreign Application Priority Data
Aug. 18, 2017 (EP) .................................. 17186763

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0004* (2013.01); *A61B 5/0031* (2013.01);
(Continued)

(58) Field of Classification Search
CPC . A61B 5/4839; A61B 5/14532; A61B 5/0004; A61B 5/0031; A61B 5/1451;
(Continued)

(56) References Cited

U.S. PATENT DOCUMENTS 7,657,297 B2 * 2/2010 Simpson .............. A61B 5/0031
600/347
9,532,738 B2 * 1/2017 Delbeke ............. A61B 5/14532
(Continued)

FOREIGN PATENT DOCUMENTS

WO 2005/006969 A1 1/2005
WO 2017/058806 A1 4/2017

OTHER PUBLICATIONS

Joshua J Meidenbauer et al: "The glucose ketone index calculator: a simple tool to monitor therapeutic efficacy for metabolic management of brain cancer", Nutrition & Metabolism, Biomed Central. London, GB, vol. 12, No. 1, Mar. 11, 2015 (Mar. 11, 2015), p. 12, XP021218198, ISSN: 1743-7075, DOI: 10.1186/12986-015-0009-2.

*Primary Examiner* — Yi-Shan Yang
*Assistant Examiner* — Kyle W. Kretzer
(74) *Attorney, Agent, or Firm* — N.V. Nederlandsch Octrooibureau

(57) ABSTRACT

The present invention relates to a personal health monitoring system including an implantable sensor and a monitoring device. The present invention further relates to a multiple user health monitoring system including a plurality of such personal health monitoring systems. The present invention further relates to a method of monitoring the biological parameters of at least one user.

16 Claims, 17 Drawing Sheets

(51) Int. Cl.
    *A61B 5/1459*     (2006.01)
    *G16H 50/30*     (2018.01)
    *A61B 5/1473*     (2006.01)

(52) U.S. Cl.
    CPC ........ *A61B 5/1451* (2013.01); *A61B 5/14546* (2013.01); *A61B 5/1459* (2013.01); *A61B 5/7275* (2013.01); *G16H 50/30* (2018.01); *A61B 5/1473* (2013.01)

(58) Field of Classification Search
    CPC . A61B 5/14546; A61B 5/1459; A61B 5/7275; A61B 5/1473; A61B 5/0015; A61B 5/02438; A61B 5/155; G16H 50/30; G16H 20/17; A61M 5/14276; A61M 2205/3576; A61M 2230/201
    See application file for complete search history.

(56) References Cited

U.S. PATENT DOCUMENTS

| | | |
|---|---|---|
| 2013/0137952 A1 | 5/2013 | McCann et al. |
| 2013/0197332 A1* | 8/2013 | Lucisano ........... A61B 5/14542 600/364 |
| 2014/0012117 A1 | 1/2014 | Mensinger et al. |
| 2014/0124384 A1 | 5/2014 | Gerber et al. |
| 2014/0350369 A1* | 11/2014 | Budiman ............ A61B 5/7282 702/19 |
| 2015/0289821 A1* | 10/2015 | Rack-Gomer ....... A61B 5/7435 600/300 |
| 2016/0066843 A1* | 3/2016 | Mensinger .............. G16H 40/63 600/365 |
| 2016/0328991 A1* | 11/2016 | Simpson ............ G09B 19/0092 |

\* cited by examiner

Health monitoring system comprising remote server

PERSONAL HEALTH MONITORING SYSTEM, MULTIPLE USER HEALTH MONITORING SYSTEM, AND METHOD

FIELD OF THE INVENTION

The present invention relates to a personal health monitoring system comprising an implantable sensor and a monitoring device. The present invention further relates to a multiple user health monitoring system comprising a plurality of such personal health monitoring systems. The present invention further relates to a method of monitoring the biological parameters of at least one user.

BACKGROUND ART

A personal health monitoring system is for example known from U.S. Pat. No. 8,718,943, which describes a health-monitoring device which assesses the health of a user based on levels of two analytes in a biological fluid. A first analyte that is utilized to assess a user's health is a fat metabolism analyte, such as ketones, free fatty acids and glycerol, which is indicative of fat metabolism. A second analyte that is utilized is a glucose metabolism analyte, such as glucose. The levels of the two analytes are used to assess insulin sensitivity, to detect both recent hypoglycemia and the cause of high glucose levels, and/or to guide therapeutic intervention. The dual analyte model calculates a discrepancy between an actual insulin activity level and a theoretical insulin activity level.

US 2017/0095216 A1 describes a wrist-worn biowatch providing various health monitoring functions such as blood glucose level monitoring, blood pressure detection, pulse monitoring, heart stop detection, oxygen saturation saturation monitoring, and Ketoacidosis detection. The biowatch is actively monitoring the wellness data of its wearer, and adapted to alert the user and medical professionals if such wellness data veers outside normal ranges or acceptable trends.

SUMMARY OF THE INVENTION

It is a first aim of the present invention to provide a personal health monitoring system, comprising an implantable sensor and a monitoring device, and capable of generating an improved personal health profile from the collected sensor data.

It is a second aim of the present invention to provide a multiple user health monitoring system with improved capabilities of monitoring health conditions of user groups.

It is a third aim of the present invention to provide an efficient method for monitoring biological parameters of at least one user.

It is a fourth aim of the present invention to provide to the user personalized behavioural, life-style and therapeutic advice and/or interventions, based on the monitoring of those biological parameters.

These and other aims may be achieved by the subject-matter of the independent claims.

The invention provides, according to a first aspect, a personal health monitoring system, comprising an implantable sensor and a monitoring device. The implantable sensor comprises sensing means for sensing biological parameters in bodily fluids of a user and a first wireless transceiver for transmitting sensor data containing data points which are provided by said sensing means upon sensing said biological parameters. The sensed biological parameters comprise at least a glucose concentration and a ketone bodies concentration in said bodily fluids, such that said sensor data comprises at least glucose concentration data points and ketone bodies concentration data points. The monitoring device comprises a second wireless transceiver for communicating with said first wireless transceiver to receive said sensor data and processing means for processing said sensor data, wherein said processing means is equipped with an algorithm which is executable on said processing means and which, when executed, is provided for performing the following steps: determining first trends in said glucose concentration data points and second trends in said ketone bodies concentration data points; and generating a personal health profile of the user.

The personal health monitoring system according to the invention senses and processes at least glucose and ketone bodies concentrations in bodily fluids.

The personal health monitoring system according to the invention uses the algorithm to analyse the sensor data. In preferred embodiments according to the invention, the algorithm is provided for detecting trends in sets of data points, and correlating trends of different sets of data points with each other. In this way, trends are detectable which are personal, i.e. specific to the user carrying the implanted sensor. Likewise, correlations between the trends in different biological parameters can be determined in a personal way, such as for example a normal evolution of glucose and ketones concentration for that user during the night or a normal evolution of glucose and ketones concentration for that user after a certain meal or a certain activity, etc. In this way, the personal health monitoring system according to the invention may be capable of "learning" for example which are normal evolutions of the biological parameters of the user and which are not normal and include this information in the personal health profile which it generates for the user. This information can then be further used by the system to for example make predictions, issue warnings, etc. In preferred embodiments according to the invention the algorithm of the monitoring device is provided for performing the following steps: determining first trends in said glucose concentration data points and second trends in said ketone bodies concentration data points; detecting first user dependent correlations between said first trends and said second trends, and generating a personal health profile of the user based on said first user dependent correlations.

In embodiments according to the invention, the personal health monitoring system may be provided for sensing and/or processing at least one of the following additional parameters: heart rate, heart rate variability, body temperature, urea, lactate, pH, fructosamine, oxaloacetate and/or hydration level, preferably lactate and/or heart rate. It has been found that by taking one or more of these parameters into account, detecting trends and possibly correlations with the trends in other biological parameters, a further improved personal health profile may be achieved.

In embodiments according to the invention, the monitoring device may comprise a display for displaying the personal health profile. In embodiments, the monitoring device may be a mobile terminal such as a smart phone, tablet, smart watch or other wearable device. In embodiments, the monitoring device may be a dedicated monitoring device which is specifically designed for the purpose of communicating with the implantable sensor and generating the personal health profile. In embodiments the monitoring device may be provided for generating and/or communicating to the user personalized behavioural, life-style and therapeutic suggestions and actions, based on the monitoring of biological parameters. In embodiments, the monitoring device may be provided for generating instructions for a controller of an insulin pump or may form part of an insulin pumping device. In embodiments, the monitoring device may be an ensemble of one or more devices.

In embodiments according to the invention, the algorithm of the monitoring device may be provided for combining the sensor data with metadata (such as gender, age, BMI, location data, calories intake data, activity data, agenda information, information on periods, method of anticonception, pregnancy, stress level and/or user habit information) upon generating the personal health profile. In case a mobile terminal is used as monitoring device, any metadata generated by means of applications running on the mobile terminal itself may be used for this purpose.

The implantable sensor is capable of continuous monitoring of biological parameters. The term 'continuous' or 'continuously' in relation to the invention should be construed as meaning 'regularly without requiring regular user intervention', the sampling rate can be a fixed number of measurements per time frame or varied by an integrated controller. In embodiments according to the invention, the implantable sensor may comprise an integrated controller which is provided for controlling the sensing means at a variable sampling rate. In embodiments, the integrated controller may be provided for detecting a variability level in said sensor data and adapting said variable sampling rate according to said detected variability level, for example by reducing the sample rate if a low variability level (beneath a certain threshold) is detected. In other embodiments, the sampling rate may also be controlled by the monitoring device. By reducing the sampling rate, for example when it is expected that the sensor data will not vary much over a longer period of time, energy consumption of the sensing means of the implanted sensor can be reduced and battery life can possibly be extended.

In embodiments according to the invention, the implantable sensor may comprise a rechargeable battery and/or components for wireless energy transfer, such that recharging can occur without having to remove the (implanted) sensor.

The invention provides, according to a second aspect, which may be combined with the other aspects and embodiments described herein, a multiple user health monitoring system which comprises a plurality of the personal health monitoring systems as described above. The multiple user health monitoring system comprises a remote server system which is provided for collecting the personal health profiles generated by the plurality of personal health monitoring systems. As a result of the self-learning capabilities of the individual personal health monitoring systems, the collected information can efficiently be used to generate e.g. reports, statistics, etc. of user groups.

The invention provides, according to a third aspect, which may be combined with the other aspects and embodiments described herein, a method for monitoring the biological parameters of at least one user. The method, and embodiments thereof, comprise substantially the steps as have already been described above in relation to the personal health monitoring system according to the invention.

BRIEF DESCRIPTION OF THE DRAWINGS

The present invention will be discussed in more detail below, with reference to the attached drawings.

DESCRIPTION OF EMBODIMENTS

Figure 1:
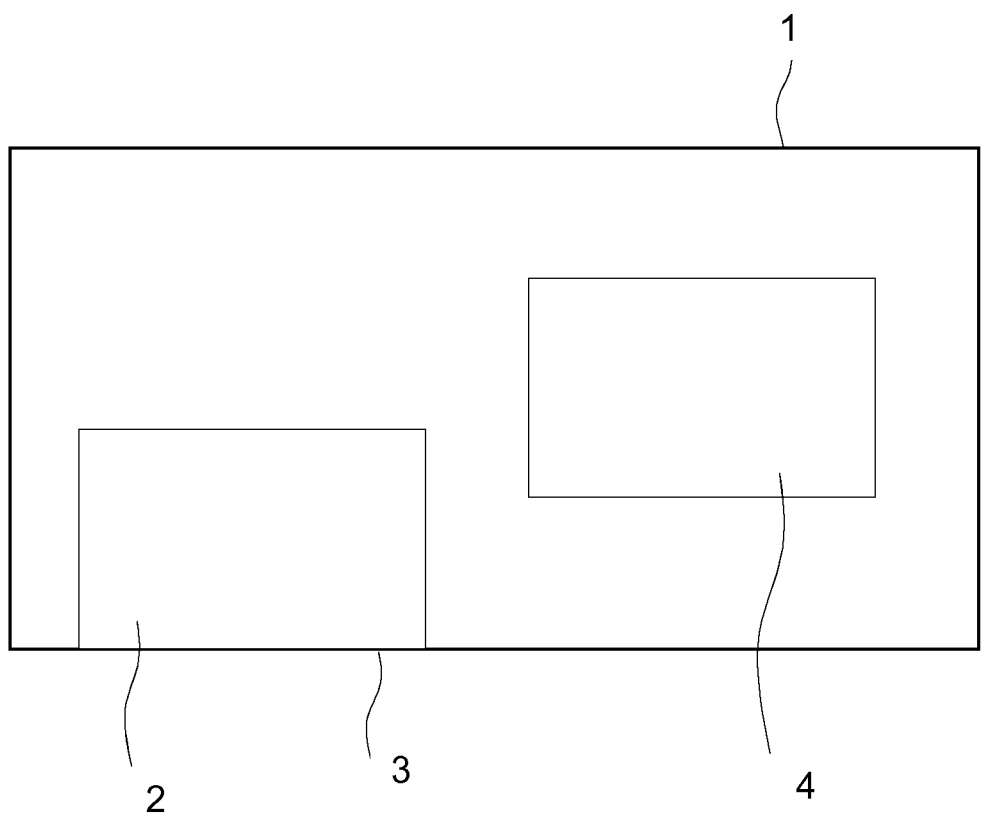
FIG. 1 shows an embodiment of the implantable sensor comprising sensor housing 1, sensing means 2, sensor housing adapted to sensing means 3 and a wireless transceiver 4.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

Whenever in this document reference is made to an 'implantable' sensor, this should be construed to mean any sensor capable of in vivo measurements of one or more biological parameters in an animal or human. The implantable sensor may be located subcutaneous, intramuscular, intravascular, ocular such as in or attached to the cornea, in or attached to an organ, in or attached to the digestive tract or in or attached to a body cavity such as mouth, eye or ear. In a preferred embodiment the implantable sensor is a subcutaneous sensor.

Figure 19:
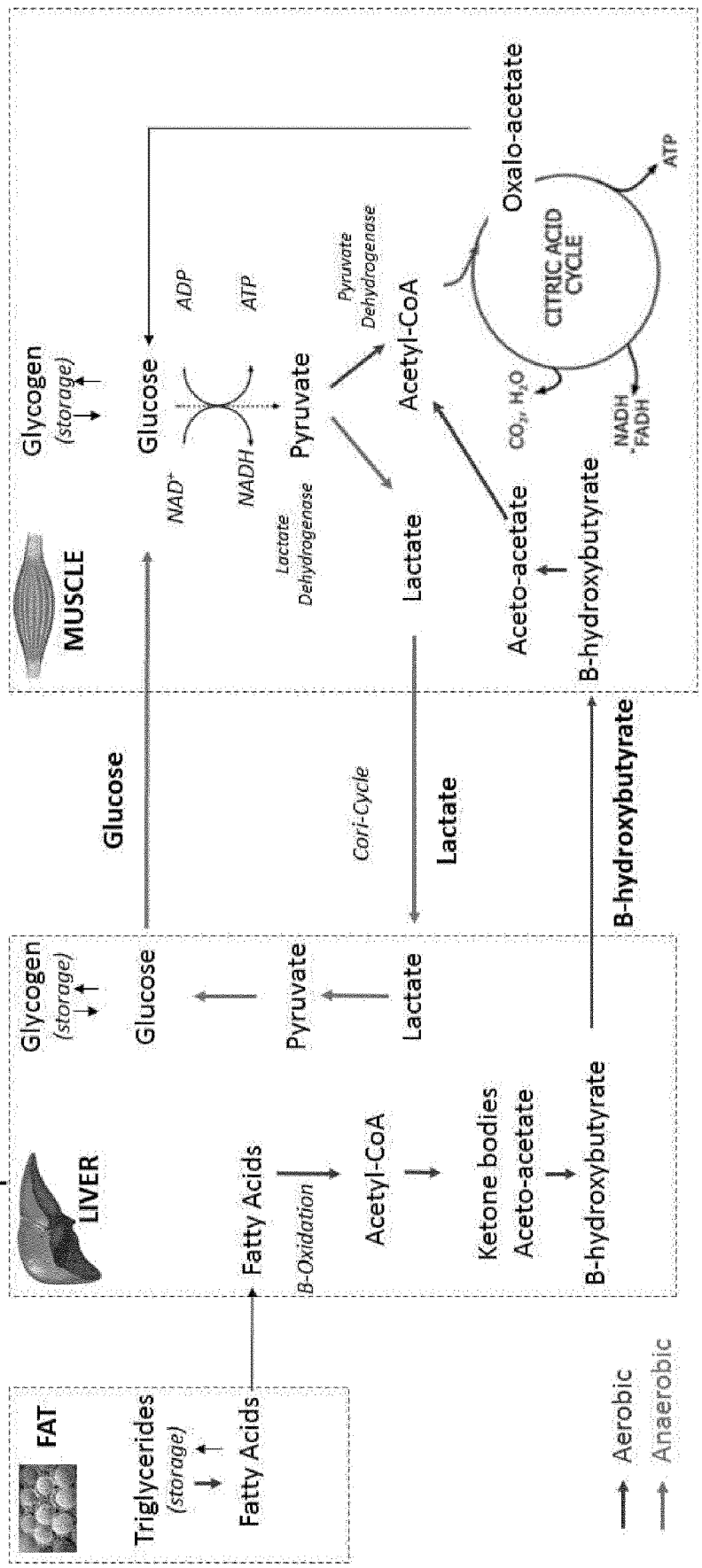
FIG. 19 is a schematic representation of the relationship between the fat metabolism and glucose metabolism.

The fat metabolism and the glucose metabolism are two groups of biochemical processes which are responsible for most of the energy generation and consumption in mammals. They are also responsible for the formation, breakdown and interconversion of biologically important molecules. FIG. 19 is a schematic representation of the relationship between fat metabolism and glucose metabolism, showing important metabolites such as ketone bodies, oxalo-acetate and lactate.

The measurement of a fat metabolism analyte, such as ketone bodies, is indicative of fat metabolism.

Ketosis in humans is a nutritional process characterised by serum concentrations of ketone bodies over 0.5 mM, with low and stable levels of insulin and blood glucose. Long-term ketosis may result from fasting or staying on a low-carbohydrate diet (ketogenic diet), and deliberately induced ketosis can be a lifestyle choice or be used as a medical intervention for various conditions, such as intractable epilepsy, and the various types of diabetes. Ketosis can also occur in animals, for example in dairy cattle during the first weeks after giving birth to a calf or to sheep in pregnancy toxemia.

Ketoacidosis is a pathological metabolic state marked by extreme and uncontrolled ketosis caused by, for example, alcohol, starvation or diabetes. In ketoacidosis, the body fails to adequately regulate ketone production causing such a severe accumulation of keto acids that the pH of the blood is substantially decreased, eventually leading to coma and death.

Monitoring ketone bodies in a mammal is thus expected to provide essential information for subjects at risk of ketosis because of medical, dietary or lifestyle conditions.

The measurement of a glucose metabolism analyte, such as glucose, is indicative of glucose metabolism.

Hypoglycaemia, also known as low blood sugar, is a condition characterized by blood sugar levels below normal levels. This may result in a variety of symptoms including clumsiness, trouble talking, confusion, loss of consciousness, seizures, or death. A feeling of hunger, sweating, shakiness, and weakness may also be present. Hypoglycaemia may be present as a consequence of medical conditions (such as diabetes), a side-effect of a medical treatment, dietary or lifestyle conditions.

Hyperglycaemia, also known as high blood sugar, is a condition characterized by blood sugar levels above normal levels. Acute hyperglycaemia can result in polyuria, polydipsia, weight loss, sometimes with polyphagia, and blurred vision and chronic hyperglycaemia may result in a range of medical conditions such as kidney damage, neurological damage, cardiovascular damage, damage to the retina, feet and legs. Hyperglycaemia may be present as a consequence of medical conditions (such as diabetes), a side-effect of a medical treatment, dietary or lifestyle conditions.

2 hour plasma glucose (2hPG), fasting plasma glucose (FPG), random plasma glucose (PG) are widely used markers of glycemic control. Continuous glucose monitoring is the prerequisite to enable strict glycemic control, keeping blood glucose levels within a desired range, such as a range that prevents medical complications. The desired range is highly personal and may be governed by factors such as medical conditions, dietary of lifestyle choices. Even within the commonly accepted "healthy" range of 80-110 mg/dl blood glucose, the ideal blood glucose level for every individual is different.

Glycated hemoglobin, interchangeably referred to as $HbA_{1c}$ is a form of hemoglobin that is formed through exposure of hemoglobin to plasma glucose. Higher amounts of glycated hemoglobin, indicating poorer control of blood glucose levels, have been associated with cardiovascular disease, nephropathy, neuropathy, and retinopathy. Glycated hemoglobin can be estimated based on the mean glucose value over time.

Embodiments of the invention provide a personal health monitoring system, comprising an implantable sensor and a monitoring device, and capable of generating an improved personal health profile from the collected sensor data.

The health monitoring system may provide insight in the metabolic state of a user, by providing user dependent correlations between ketone bodies and glucose levels. The analysis of trends in glucose and ketone bodies levels while taking into account personal correlations may provide improved means for subjects to manage their metabolic state. For example, for patients suffering from diabetes, the change from modest hyperglycaemia to ketoacidosis can occur slowly or very rapidly, depending on the type of diabetes and the individual patient (e.g. infants vs. adults). Improved analysis of trends and prediction, taking into account individual correlations between ketone bodies and glucose levels, may be of vital importance for these patients. Patients following a ketogenic diet as (complementary) treatment of brain tumor may also benefit from the user dependent correlations between ketone bodies and glucose levels which are the object of some preferred embodiments of the personal health monitoring system of the present invention.

The ability to maintain blood glucose and ketone bodies within a desired range requires frequent measurements of glucose and ketone bodies. Each ketone bodies and glucose measurement provides information about the fat and glucose metabolism that can be used to determine the personal health profile of a subject. This subject may be a patient (e.g. suffering from diabetes) or any person seeking to monitor and improve their personal health profile.

The implantable sensor of the health monitoring system of the present invention is shown in FIG. 1 and comprises sensor housing 1, means for sensing biological parameters in bodily fluids 2, an area of sensor housing which is adapted to the sensing means 3 and a wireless transceiver 4. The implantable sensor may be capable of sensing biological parameters based on surface chemical reactions and/or by using optical means. The implantable sensor may be capable of performing a reagent-free optical analysis method. The implantable sensor may comprise biocompatible packaging in order to reduce or minimize the risk of bio-fouling.

Figure 2:
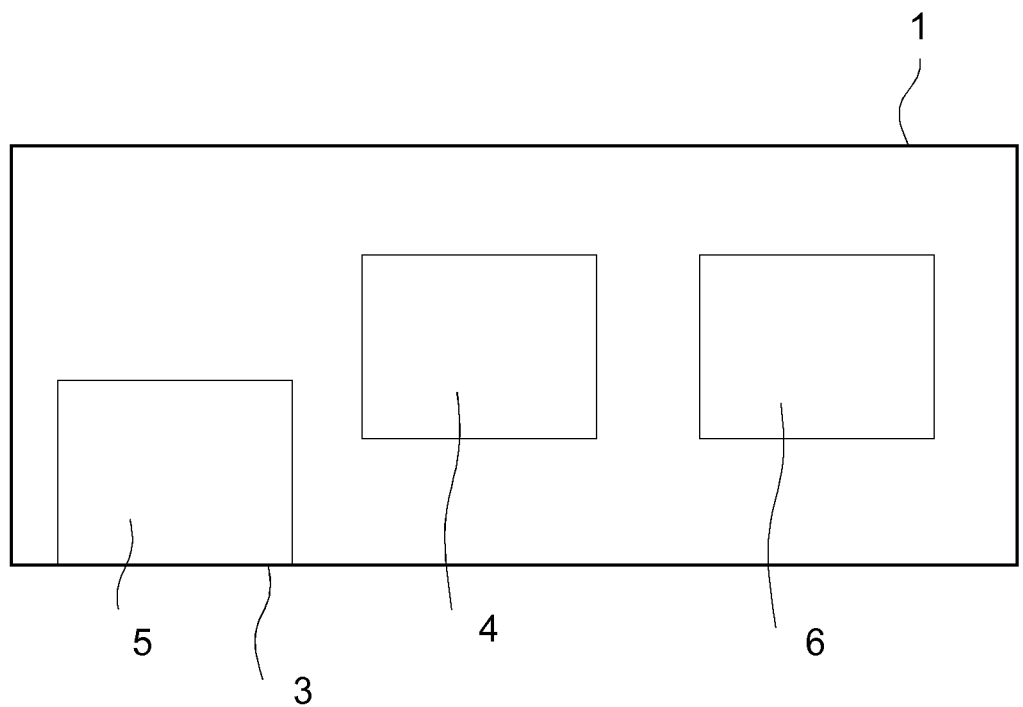
FIG. 2 shows an embodiment of the implantable sensor with optical sensing means 5 and optical processor 6.

A preferred embodiment of an implantable sensor is shown in FIG. 2 and is equipped with optical sensing means 5 and an optical processor 6 (e.g. a single-chip optical sensor) for continuous analyte monitoring. The implantable sensor comprises an advanced optical processor in the sensor, allowing advanced and optionally complex radiation processing, e.g. allowing spectral and depth-resolved processing of radiation received or guided to a measurement region.

The implantable sensor comprises means for sensing biological parameters in bodily fluids and comprises a wireless transceiver for transmitting sensor data containing data points which are provided by said sensing means upon sensing biological parameters. The implantable sensor is provided for measuring at least glucose and ketone bodies in bodily fluids. The sensing means may be as described in U.S. Pat. No. 9,532,738 B2, in particular column 11 line 15-67, which are hereby incorporated by reference.

In embodiments of the invention, the implantable sensor may be adapted for sensing biological parameters in bodily fluids wherein the bodily fluid may be interstitial fluid, ocular fluid, intermuscular fluid or peritoneal fluid. It has been found that measurements of biological parameters in the interstitial fluid present a reliable relationship with blood values, are minimally invasive and safe and present other advantages such as the elimination of the need for anticoagulants. Thus, in a preferred embodiment of the invention, the implantable sensor is a subcutaneous implantable sensor.

Figure 3:
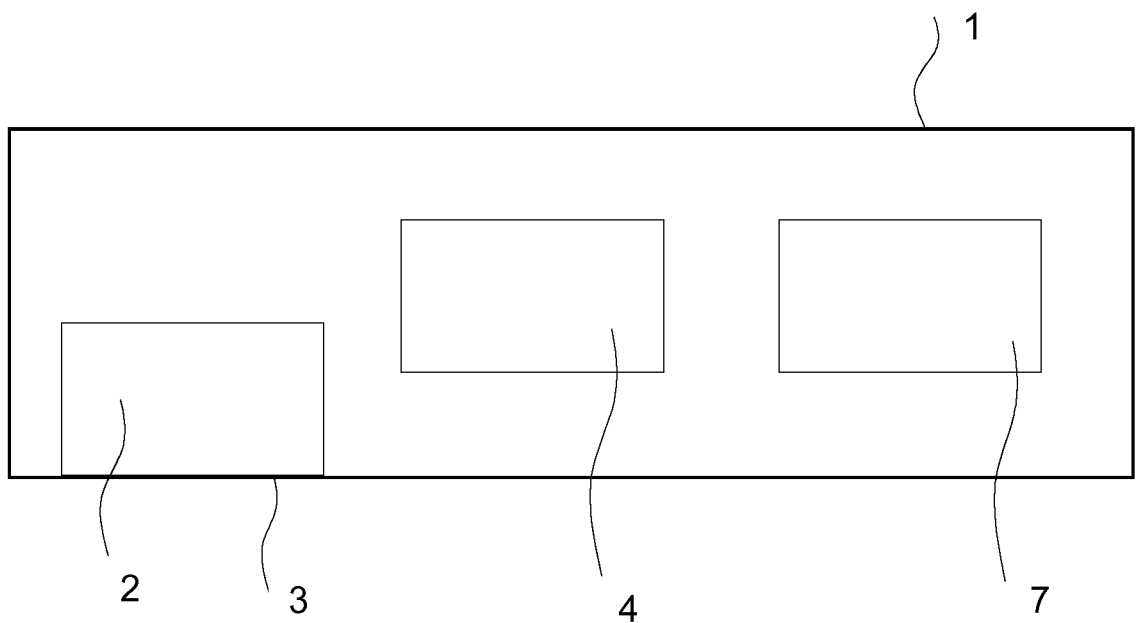
FIG. 3 shows an embodiment of the implantable sensor with components for wireless energy transfer 7.
Figure 4:
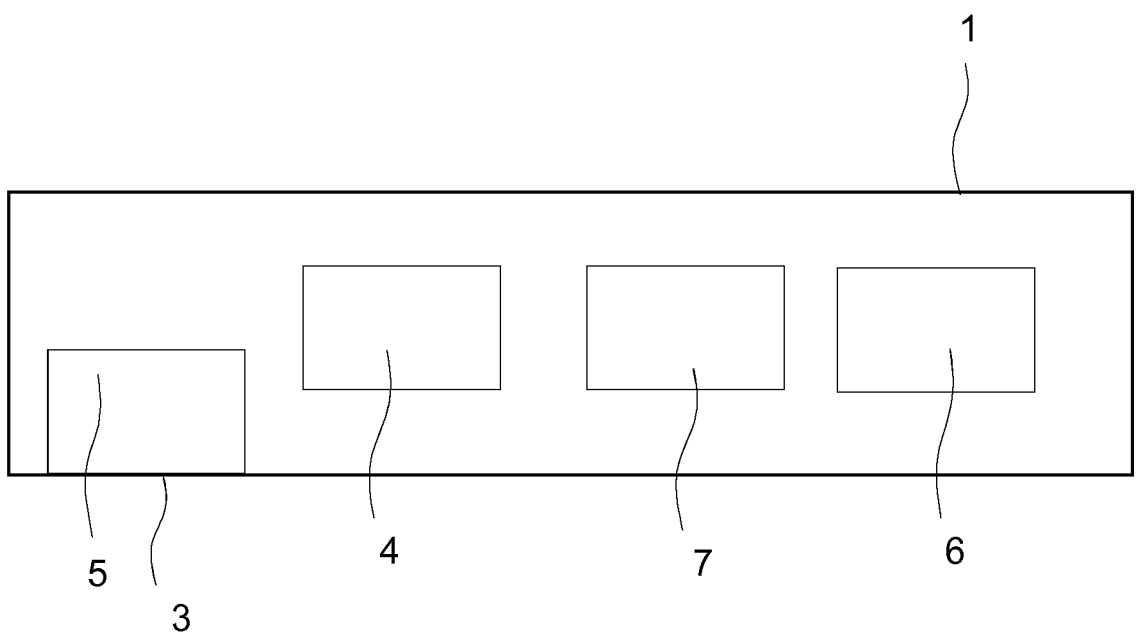
FIG. 4 shows an embodiment of the implantable sensor with components for wireless energy transfer 7 and optical sensing means 5 and optical processor 6.

In embodiments of the invention, the implantable sensor may comprise a rechargeable battery and/or components for wireless energy transfer. A preferred embodiment of an implantable sensor is shown in FIG. 3 and is equipped with components for wireless energy transfer 7. A more preferred embodiment of an implantable sensor is shown in FIG. 4 and is equipped with optical sensing means 5 and an optical processor 6 and components for wireless energy transfer 7. In a preferred embodiment, the rechargeable battery is a solid state battery.

Figure 5:
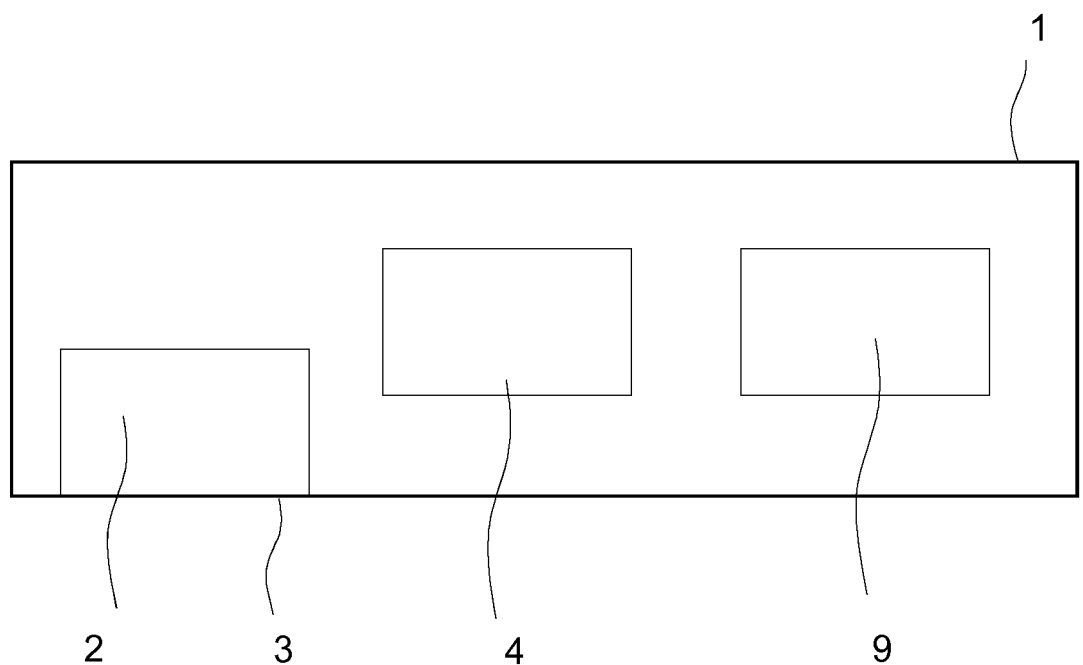
FIG. 5 shows an embodiment of the implantable sensor with processing means 9.

In embodiments of the invention, the implantable sensor may further be equipped with means for processing sensor data, wherein said processing means is equipped with an algorithm which is executable on said processing means and which is provided for converting sensor data before transmitting to the monitoring device. A preferred embodiment of an implantable sensor is shown in FIG. 5 and is equipped with a processing means 9.

The implantable sensor may further be capable of sensing heart rate, heart rate variability, body temperature, urea, lactate, pH, fructosamine, oxaloacetate and/or hydration level, preferably lactate and/or heart rate.

Figure 6:
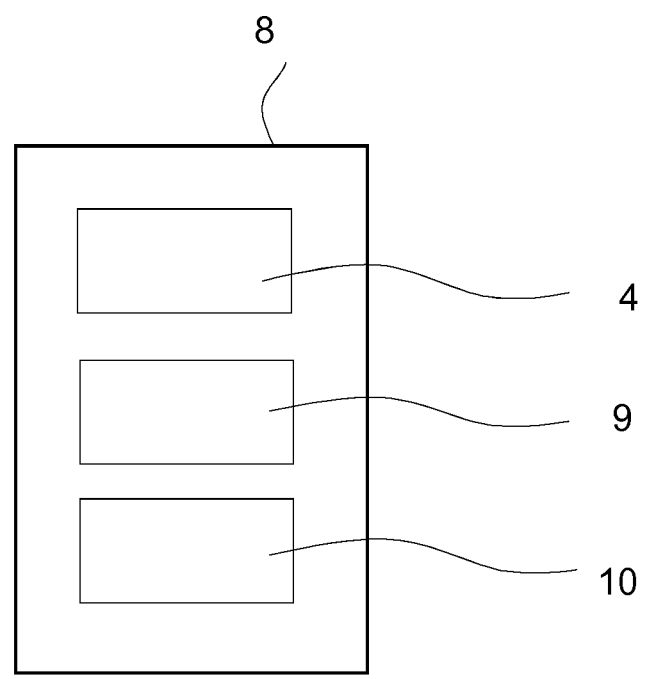
FIG. 6 shows an embodiment of the monitoring device comprising a wireless transceiver 4, monitoring device housing 8, processing means 9 and a memory 10.
Figure 11:
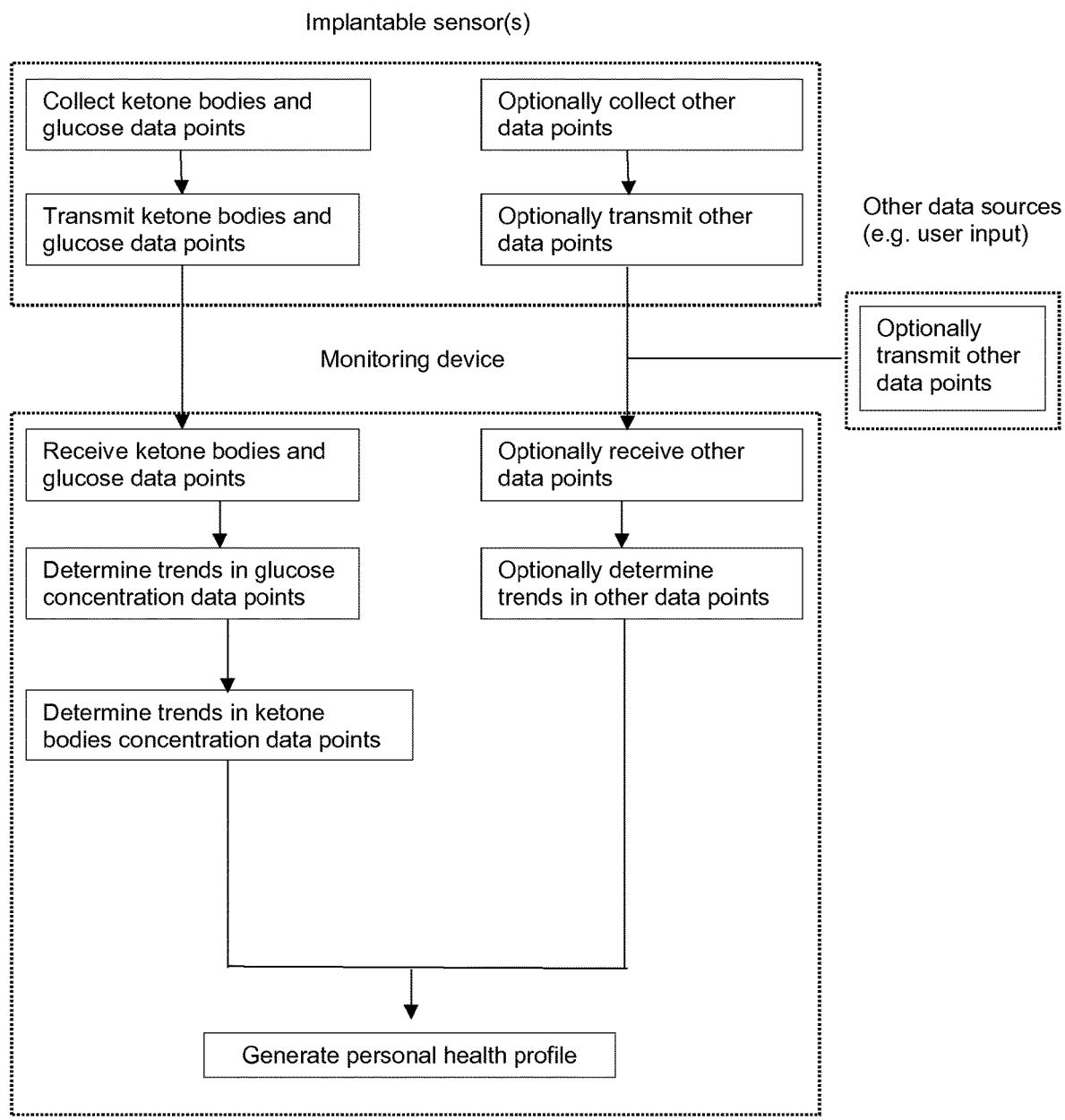
FIG. 11 shows an embodiment of the algorithm of the health monitoring system.

A preferred embodiment of a monitoring device is shown in FIG. 6 and comprises a housing 8, a wireless transceiver 4 for communicating with the wireless transceiver of the implantable sensor or other devices of the monitoring device to receive sensor data. The monitoring device further comprises processing means 9 for processing said sensor data and a memory 10 for storing data. The processing means is equipped with an algorithm, an embodiment of which is shown in FIG. 11, which is loadable into the memory 10 for execution by said processing means. The algorithm is at least provided for: determining trends in glucose concentration data points and in ketone bodies concentration data points and generating a personal health profile of the user. In embodiments according to the invention, shown in FIG. 12, the algorithm of the monitoring device may be provided for performing the following steps: determining first trends in said glucose concentration data points and second trends in said ketone bodies concentration data points; detecting first user dependent correlations between said first trends and said second trends, and generating a personal health profile of the user based on said first user dependent correlations. In a preferred embodiment of the invention the monitoring device is a smartphone. In another preferred embodiment of the invention the monitoring device is a smart watch.

Figure 7:
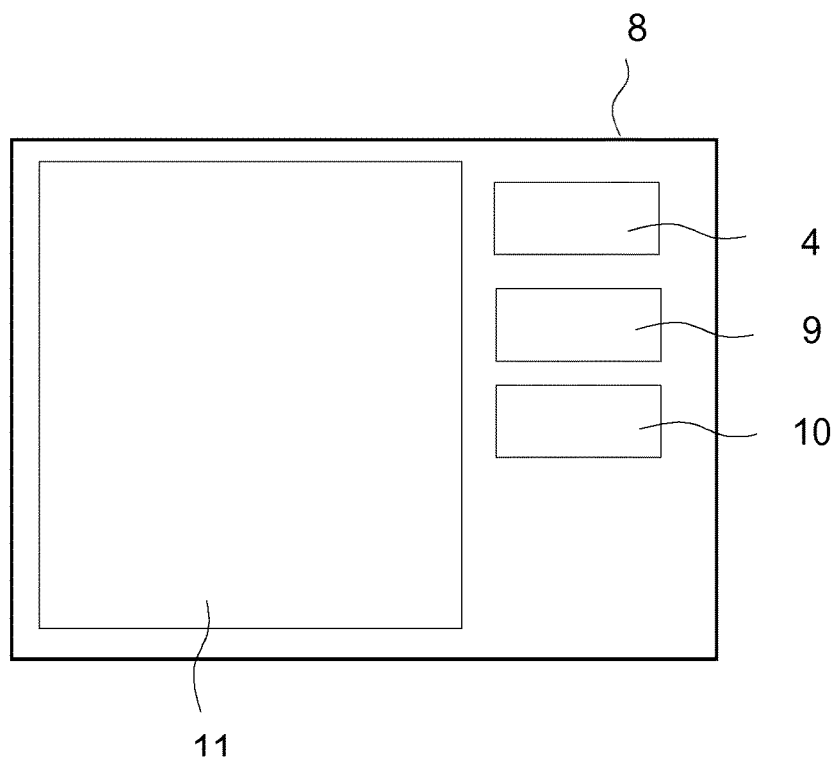
FIG. 7 shows an embodiment of the monitoring device with display 11.
Figure 8:
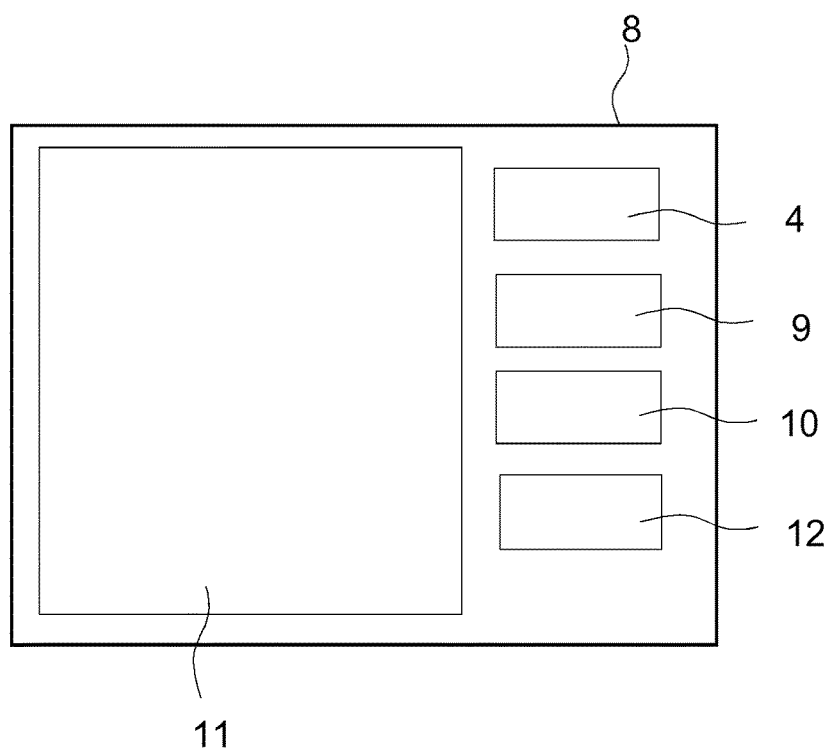
FIG. 8 shows an embodiment of the monitoring device with heart rate sensor 12.
Figure 12:
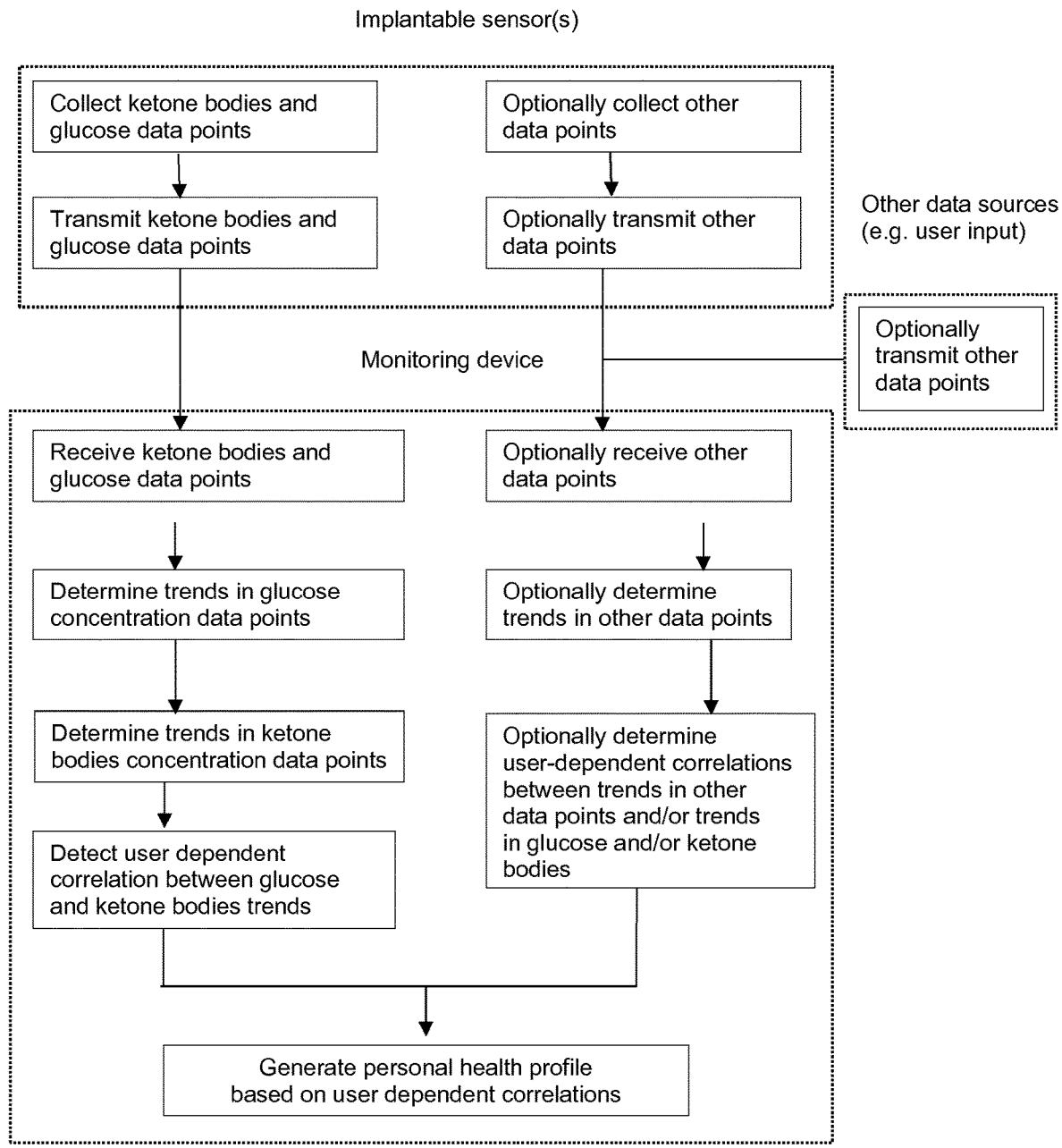
FIG. 12 shows another embodiment of the algorithm of the health monitoring system.
Figure 13:
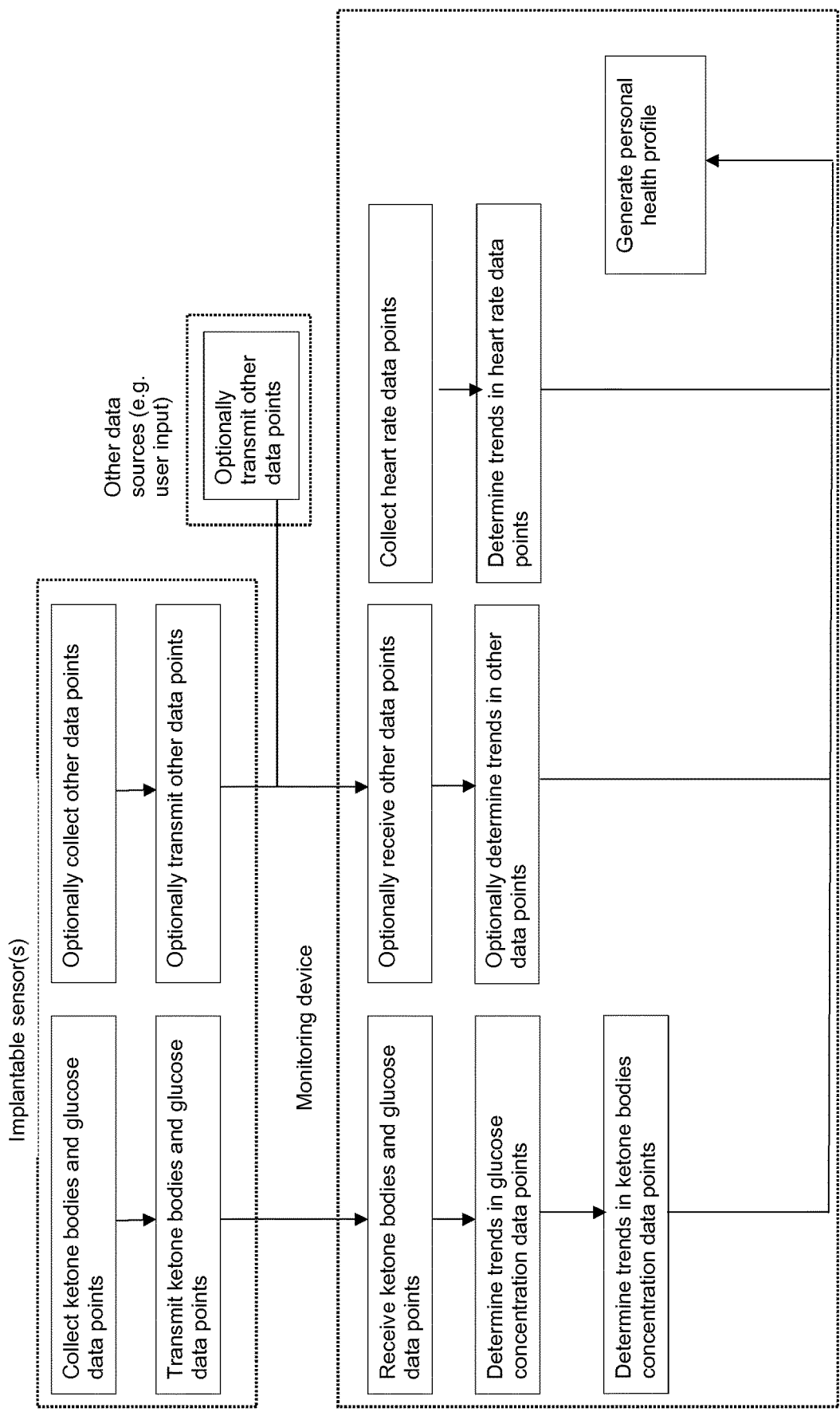
FIG. 13 shows an embodiment of the algorithm of the health monitoring system with a heart rate monitor in the monitoring device.
Figure 14:
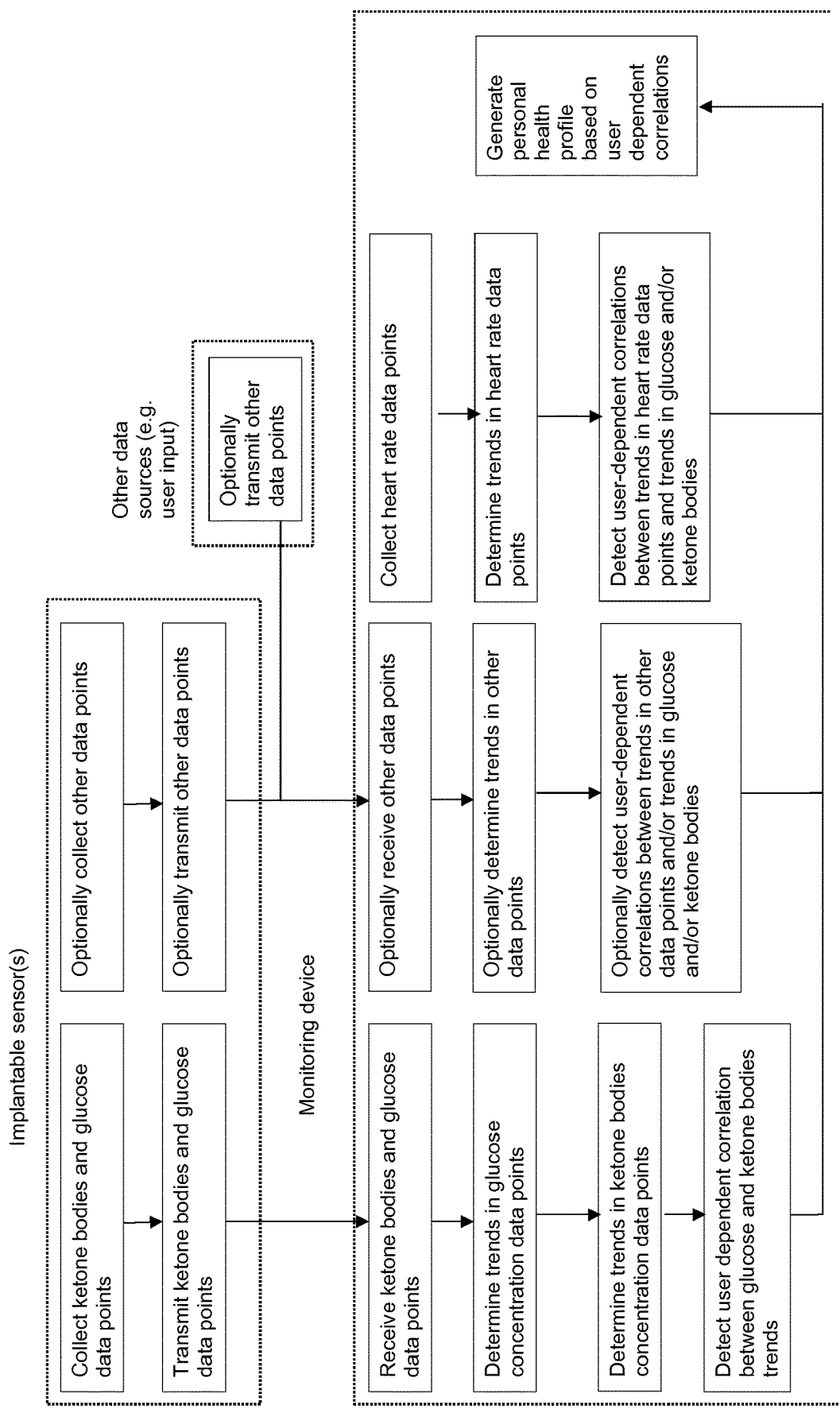
FIG. 14 shows another embodiment of the algorithm of the health monitoring system with a heart rate monitor in the monitoring device.
Figure 15:
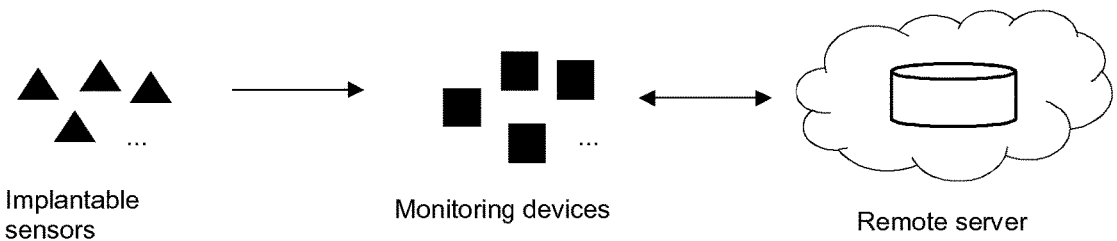
FIG. 15 shows an embodiment of the health monitoring system comprising a remote server.
Figure 16:
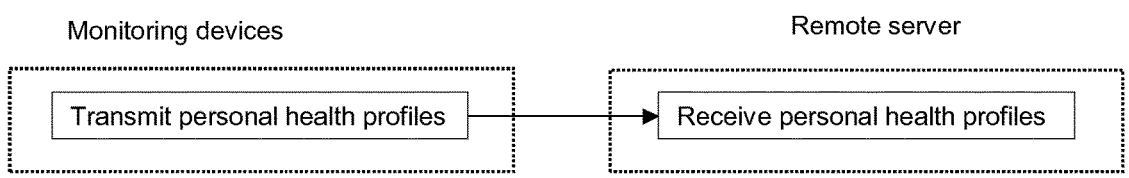
FIG. 16 shows an embodiment of the interaction of monitoring devices with a remote server.
Figure 17:
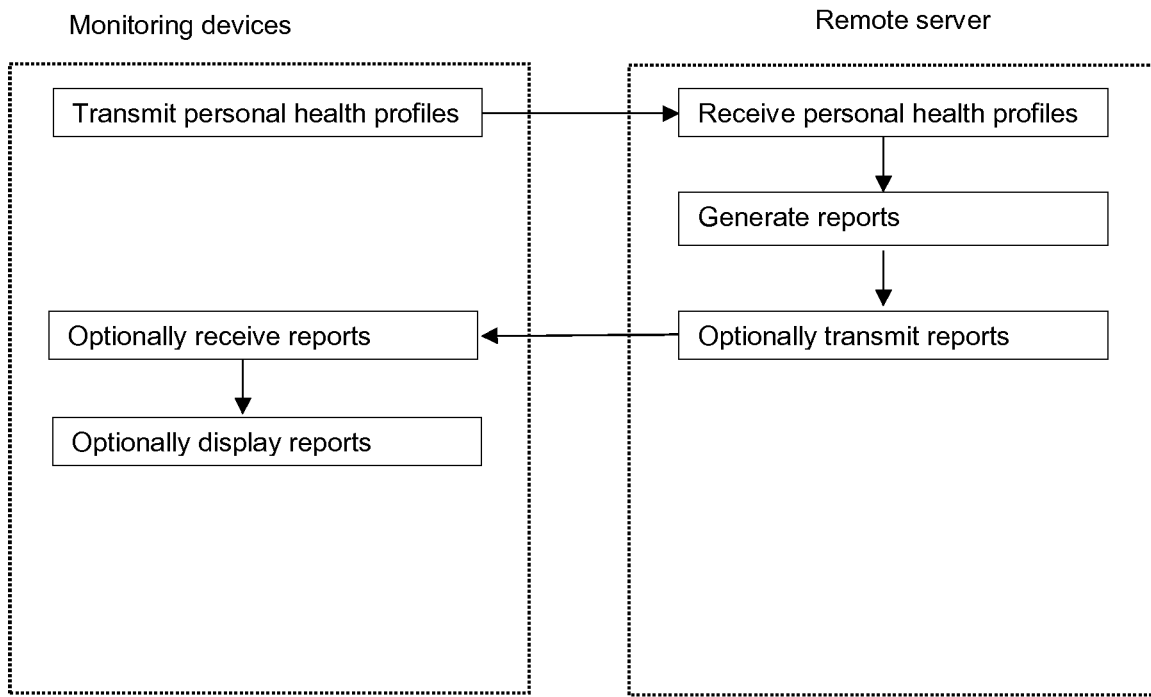
FIG. 17 shows another embodiment of the interaction of monitoring devices with a remote server.
Figure 18:
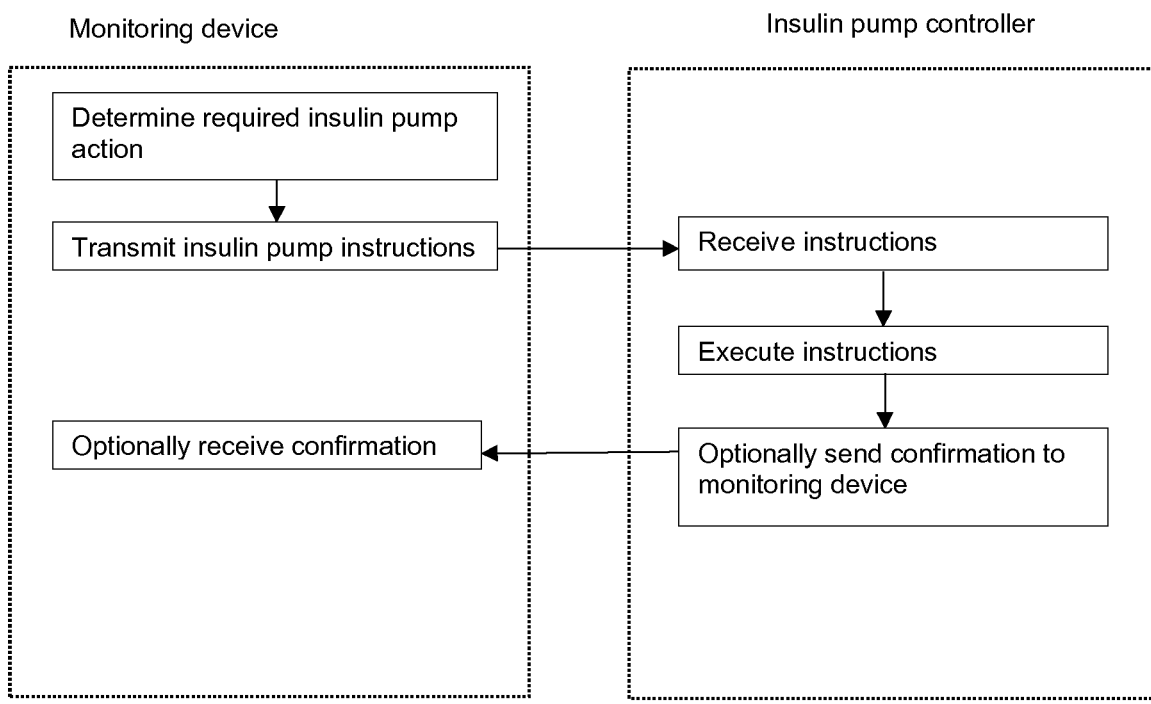
FIG. 18 shows an embodiment of the interaction of the monitoring device with an insulin pump controller.

Another embodiment of the monitoring device is shown in FIG. 7 wherein the monitoring device is equipped with a user interface, comprising a display 11 for displaying the personal health profile and interacting with the user. The monitoring device may further be provided for receiving heart rate data points from a heart rate sensor, said heart rate data points being received from the implantable sensor or any other device which is capable of providing heart rate data points. For example, in case the monitoring device is a smart watch, a heart rate sensor may be provided on board the smart watch. FIG. 8 shows a preferred embodiment of the monitoring device wherein the monitoring device is equipped with a heart rate sensor 12. The algorithm may be provided for determining trends in the heart rate data points and detecting user dependent correlations between trends in heart rate data points and trends in glucose concentration data points and/or ketone bodies concentration data points, and evaluating said user dependent correlations upon generating a personal health profile. Thus, a further improved personal health profile may be achieved. FIGS. 11 and 12 show embodiments of the algorithm wherein the heart rate data points could be received as other data points, while FIGS. 13 and 14 show embodiments of the algorithm wherein the heart rate data points are being collected by the monitoring device.

In another embodiment of the present invention the monitoring device may further be provided for receiving and processing data points of one or more of the following parameters: glycated hemoglobin, heart rate, heart rate variability, body temperature, urea, lactate, pH, fructosamine, oxaloacetate and/or hydration level, preferably lactate and/or heart rate. These parameters may be provided by the implantable sensor or any one or more additional implantable sensors and/or other device which is capable of providing data points of one or more of said parameters. The algorithm executable on the processing means may then be provided for determining trends in the data points of the one or more additional parameters (glycated hemoglobin, heart rate, heart rate variability, body temperature, urea, lactate, pH, fructosamine, oxaloacetate and/or hydration level), and generating a personal health profile. In a preferred embodiment the algorithm executable on the processing means may then be provided for determining trends in the data points of the one or more additional parameters, detecting user dependent correlations between said trends and trends in heart rate data points, trends in glucose concentration data points and/or ketone bodies concentration data points, and evaluating said user dependent correlations upon generating a personal health profile. Thus, a further improved personal health profile may be achieved. FIGS. 11 and 12 show embodiments of the algorithm wherein the glycated hemoglobin, heart rate, heart rate variability, body temperature, urea, lactate, pH, fructosamine, oxaloacetate and/or hydration level data points could be received as other data points.

In another embodiment of the present invention the monitoring device may further be provided for receiving and processing data points of one or more of the following parameters: nutritional intake such as carbohydrate intake data points, activity such as accelerometer data points and/or blood pressure data points and location such as GPS data points, agenda item data points. These parameters may be provided by the implantable sensor or any one or more additional implantable sensors and/or other device which is capable of providing data points of one or more of said parameters and/or manual user input. The algorithm executable on the processing means may then be provided for determining trends in the data points of the one or more additional parameters (nutritional intake, activity, location) and generating a personal health profile. In a preferred embodiment the algorithm executable on the processing means may then be provided for determining trends in the data points of the one or more additional parameters (nutritional intake, activity), detecting user dependent correlations between said trends and trends in heart rate data points, trends in glucose concentration data points and/or ketone bodies concentration data points, and evaluating said user dependent correlations upon generating a personal health profile. Thus, a further improved personal health profile may be achieved. FIGS. 11 and 12 show embodiments of the algorithm wherein the nutritional intake, activity, location could be received as other data points.

The glucose ketone index is a biomarker that refers to the molar ratio of circulating glucose over β-OHB, which is the major circulating ketone body. The glucose ketone index is a single value that can assess the relationship of the glucose to ketone bodies. The glucose ketone index is described in Meidenbauer et al. Nutrition & Metabolism 2015, 12:12, which is incorporated herein by reference. In another embodiment of the present invention, the monitoring device may comprise an algorithm executable on the processing means provided for determining the glucose ketone index (GKI). In a preferred embodiment the algorithm executable on the processing means may then be provided for determining trends in the glucose ketone index, detecting user dependent correlations between said trends and trends in heart rate data points, trends in glucose concentration data points and/or ketone bodies concentration data points, and evaluating said user dependent correlations upon generating a personal health profile. Thus, a further improved personal health profile may be achieved.

Figure 9:
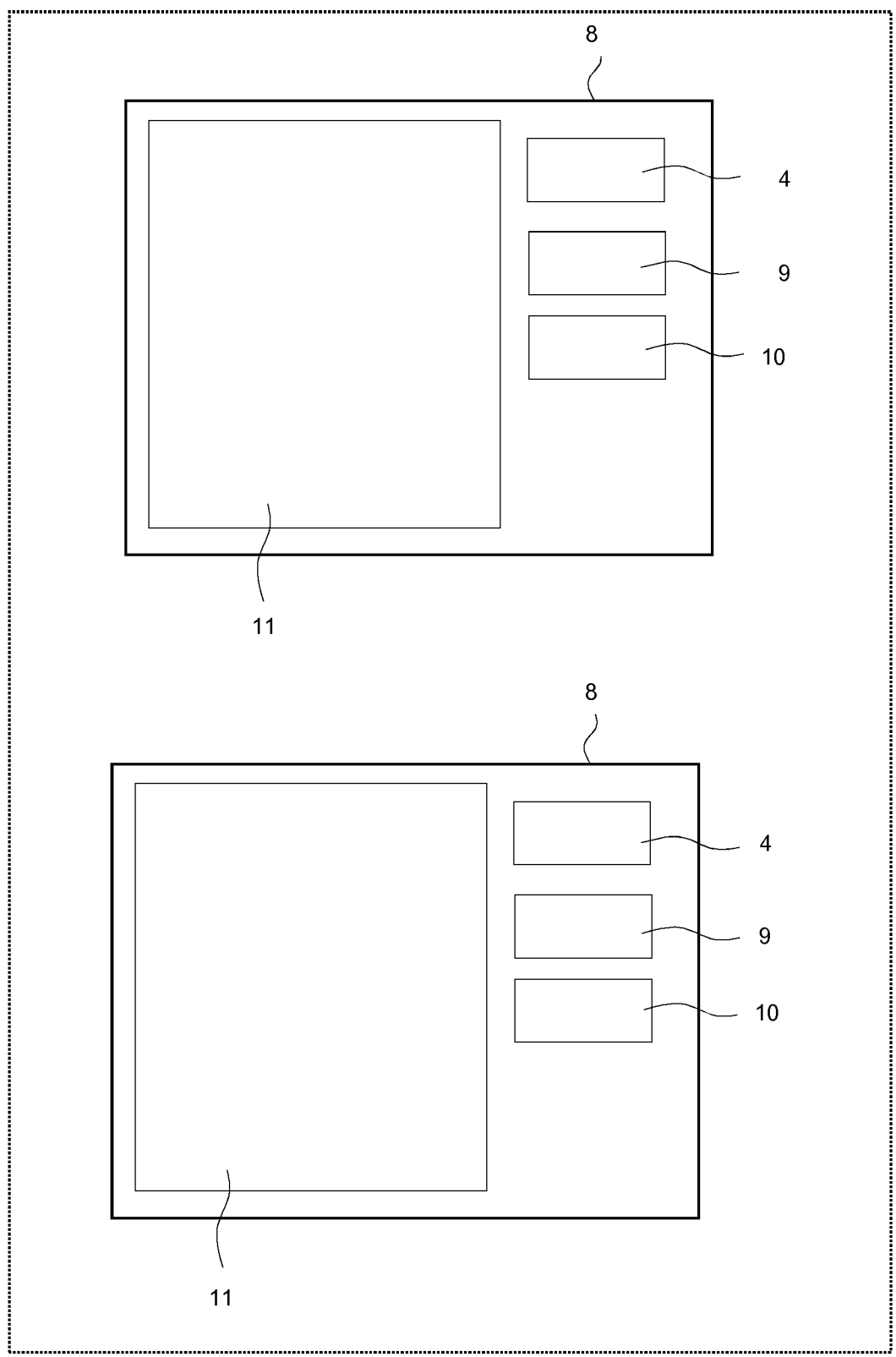
FIG. 9 shows an embodiment of the monitoring device as an ensemble of devices.
Figure 10:
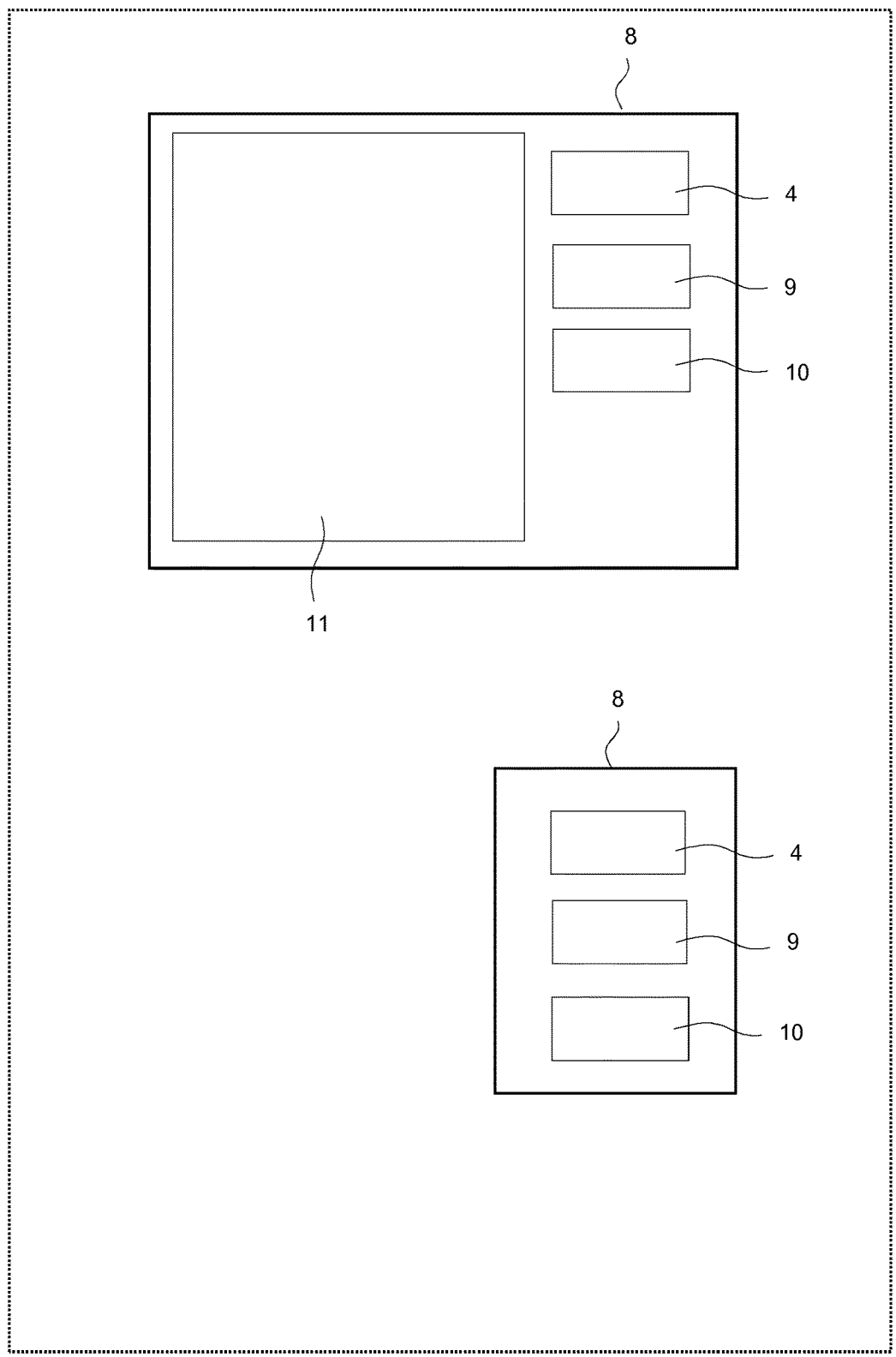
FIG. 10 shows another embodiment of the monitoring device as an ensemble of devices.

In another embodiment of the invention, different features of the monitoring device may be present on different devices. The monitoring device may thus be an ensemble of two or more devices, each device comprising a transceiver for receiving and transmitting data. FIGS. 9 and 10 show an embodiment of the invention wherein the monitoring device is an ensemble of devices. In a preferred embodiment the monitoring device comprises one or more of the following devices: a device equipped with a transceiver and a processor, a smartphone and a cloud server. In a more preferred embodiment the device equipped with a transceiver and a processor is capable of transmitting and receiving at least two different communication protocols. In embodiments, the at least two different communication protocols may be wired and/or wireless signals. In embodiments, the wireless signals may comprise signals according to different wireless bands and/or protocols such as IEEE802.11, bluetooth, cellular etc.

In another embodiment of the invention, the monitoring device may be an ensemble of two or more devices, each device comprising a transceiver for receiving and transmitting data, wherein two or more devices are each equipped with a processing means and an algorithm executable on the processing means. In a preferred embodiment of the invention, the algorithm of each device is provided performing one or more steps necessary for generating a personal health profile according to the invention.

In embodiments the monitoring device may be provided for generating and/or communicating to the user personalized behavioural, life-style and therapeutic suggestions and actions, based on the monitoring of biological parameters. In embodiments, the monitoring device may be provided for generating instructions for a controller of an insulin pump or may form part of an insulin pumping device.

In embodiments the monitoring device may be an ensemble of two or more devices wherein each device comprising a transceiver for receiving and transmitting data, wherein two or more devices are each equipped with a processing means and an algorithm executable on the processing means wherein the algorithm of each device is provided for performing one or more steps necessary for generating and/or communicating to the user personalized behavioural, life-style and therapeutic suggestions and actions, based on the monitoring of biological parameters. In a preferred embodiment of the invention the monitoring device is an ensemble of devices which includes an insulin pumping device and/or controller of an insulin pump. In a more preferred embodiment of the invention the monitoring device is an ensemble of devices which includes an insulin pumping device and/or controller of an insulin pump and a smartphone.

In a preferred embodiment of the invention, the monitoring device is an ensemble of devices which includes a remote server. In a more preferred embodiment of the invention, the monitoring device is an ensemble of devices which includes a remote server wherein the remote server is equipped with algorithm which is executable on said remote server and provided for performing one or more steps necessary for generating and/or communicating to the user a personal health profile and/or personalized behavioural, life-style and therapeutic suggestions and actions, based on the monitoring of biological parameters. In another preferred embodiment of the invention, the monitoring device is an ensemble of devices which does not include a remote server.

A preferred embodiment of the present invention, shown in FIG. 11 provides a multiple user health monitoring system comprising a plurality of personal health monitoring systems and further comprising a remote server system which is provided for collecting the personal health profiles generated by the plurality of personal health monitoring systems. In another embodiment, the remote server system is equipped with a further algorithm which is executable on said remote server system and provided for generating reports based on said collected personal health profiles. The reports may include personal recommendations optionally sent back to the monitoring device and displayed to the user, anonymous statistical data from a group of users or instructions for other devices such as an insulin pump. The reports may also include instructions for the monitoring device to be relayed to the implantable sensor.

The invention also provides a method to generate a personal health profile comprising measuring glucose concentration data points and ketone bodies concentration data points using an implantable sensor, transmitting glucose concentration data points and ketone bodies concentration data points to a monitoring device, determining first trends in said glucose concentration data points and second trends in said ketone bodies concentration data points, detecting first user dependent correlations between said first trends and said second trends, and generating a personal health profile of the user based on said first user dependent correlations.

In embodiments the monitoring device may be provided for generating and/or communicating to the user personalized behavioural, life-style and therapeutic advice and/or interventions, based on the monitoring of biological parameters. In a preferred embodiment of the present invention the behavioural, life-style and therapeutic suggestions and actions may be one or more of the following: nutritional advice, emergency care advice, therapeutic advice and/or interventions, insulin pump controller instructions.

Examples

FIGS. 19-23 show a group of embodiments of the invention that may for example be provided for detecting and correlating trends as follows.

Figure 20:
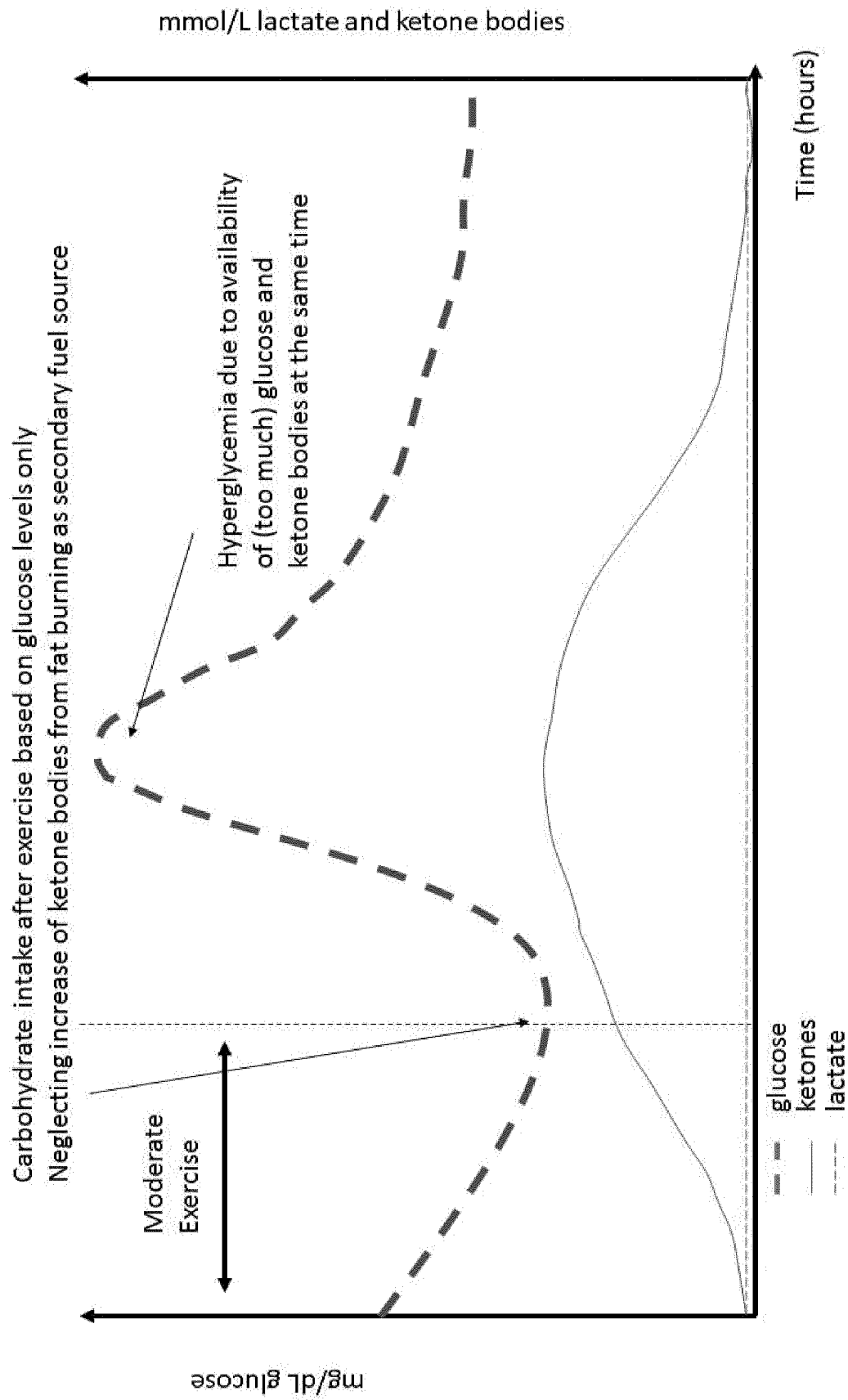
FIG. 20 shows a diagrammatic representation of an example of a glucose and ketone trend after moderate exercise.

Examples of useful glucose, ketone and optionally lactate concentration trends to be detected are as follows:

FIG. 20 shows an example of moderate ketones and hypoglycaemia resulting in the generation of a personal health profile and recommendations and/or instructions comprising "You had a good exercise, please moderate carbohydrate intake (as compared to what you would take based on your current glucose levels) since ketones are available as secondary fuel source for the next 2-3 hours."

Figure 21:
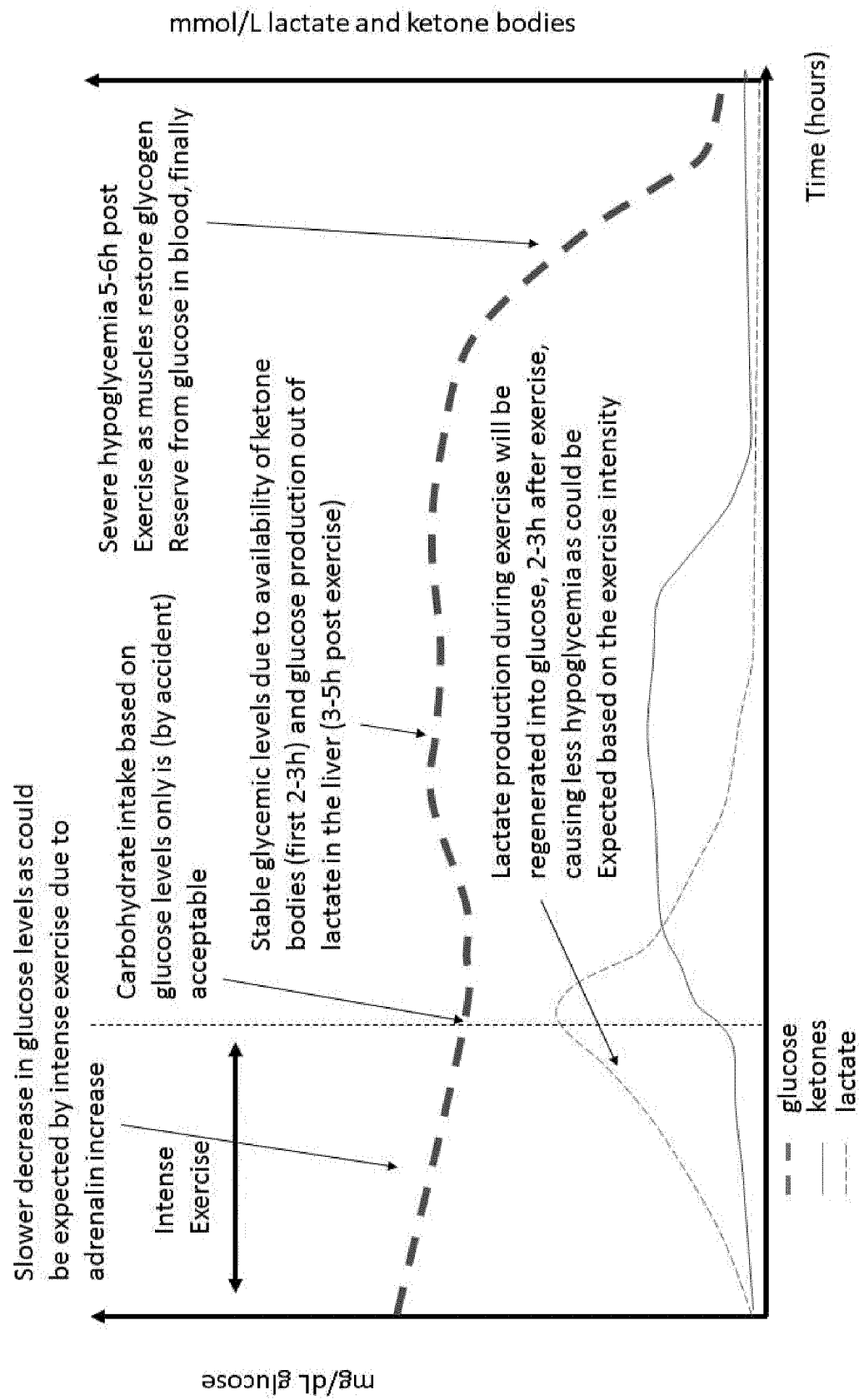
FIG. 21 shows a diagrammatic representation of an example of a glucose and ketone trend after intense exercise.

FIG. 21 shows an example of slow decrease in glucose, increase in lactate and increase in ketone bodies indicate intense exercise, resulting in the generation of a personal health profile and recommendations and/or instructions comprising: "You had a good exercise, please moderate carbohydrate intake (as compared to what you would take based on your current glucose levels) since lactate and ketones are available as fuel source for the next 4-5 hours. Ensure you take carbohydrates in 4-5 h in order to prevent late post-exercise (recovery) hypoglycaemia."

Figure 22:
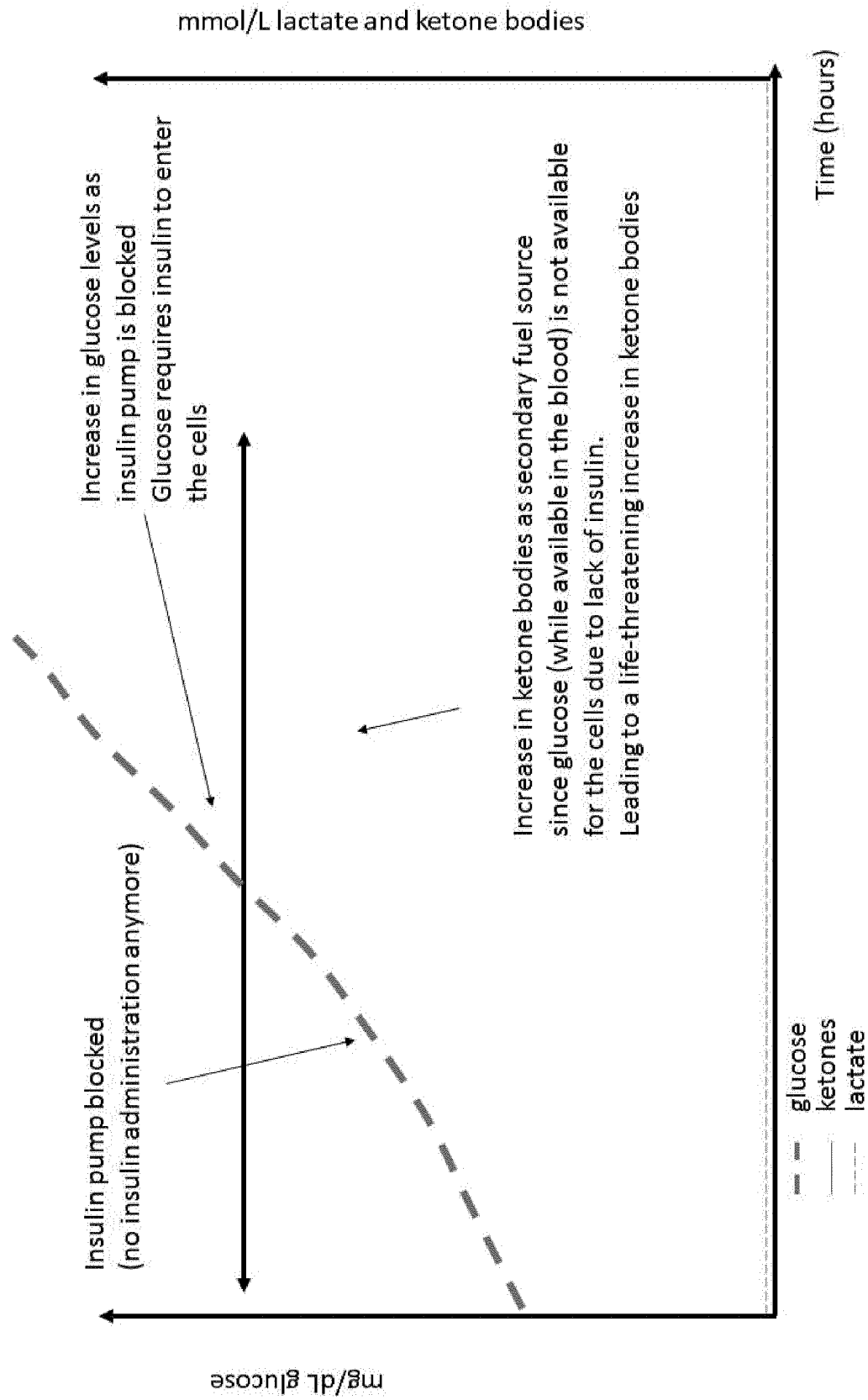
FIG. 22 shows a diagrammatic representation of an example of a glucose and ketone trend after insufficient insulin delivery.

FIG. 22 shows an example of high ketones and hyperglycaemia resulting in the generation of a personal health profile and recommendations and/or instructions comprising: "Possible insulin pump defect (insufficient insulin delivery), danger for ketoacidosis!, drink water and consult emergency medical care."

Figure 23:
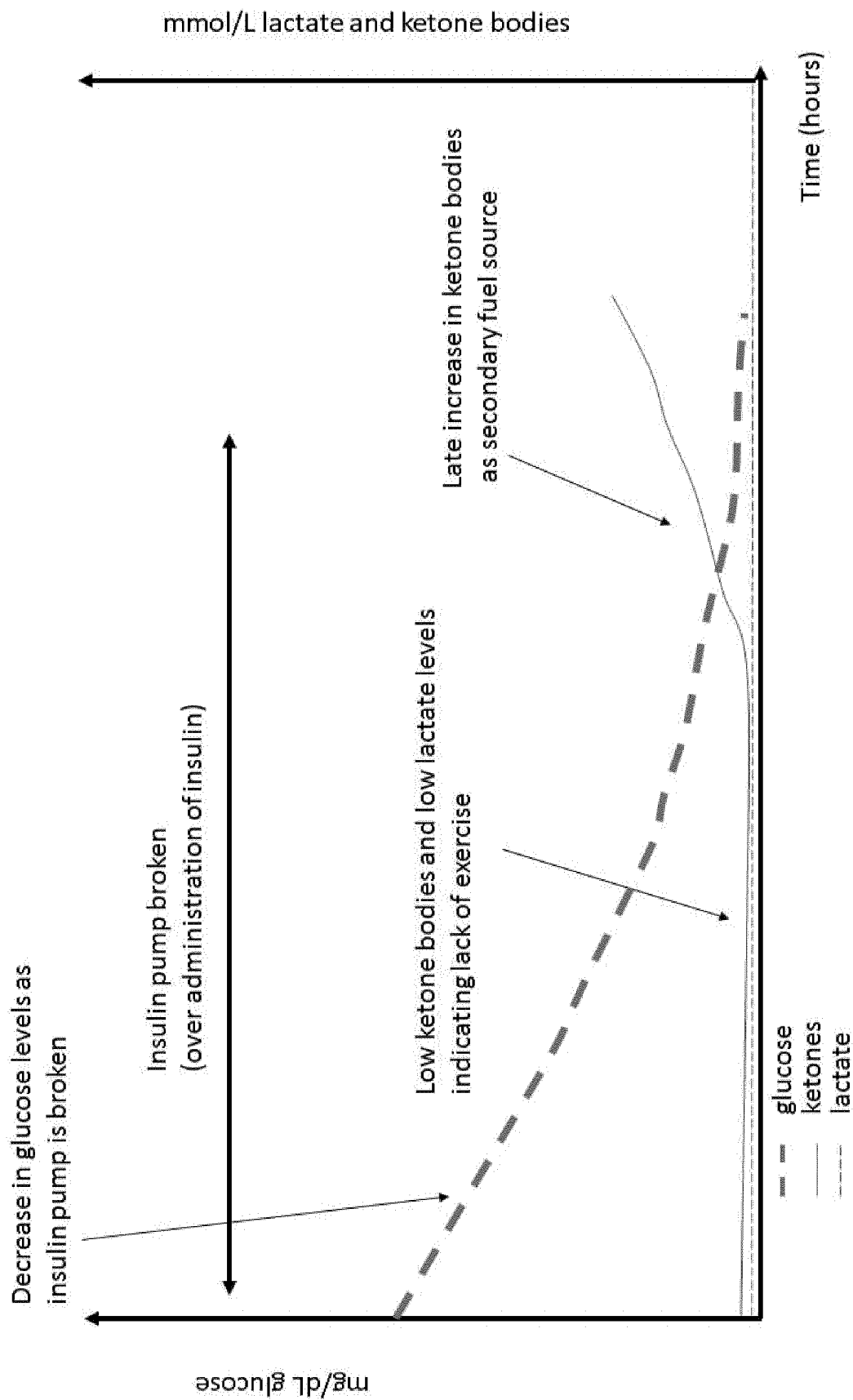
FIG. 23 shows a diagrammatic representation of an example of a glucose and ketone trend after excessive insulin delivery.

FIG. 23 shows an example of low ketones and hypoglycaemia resulting in the generation of a personal health profile and recommendations and/or instructions comprising: "Possible insulin over-administration or insulin pump defect (excessive insulin delivery), please increase carb intake and/or check your pump."

Useful heart rate trends to be detected are for example:

Loss in heart rate variability in combination with progressive hypoglycaemia resulting in the generation of a personal health profile and recommendations and/or instructions comprising: Important hypoglycaemia—danger for conscious loss, take immediately fast acting carbohydrates and consult emergency medical care.

Useful user dependent correlations are for example:

Known response rate of ketone concentration and glucose concentration to insulin administration and carbohydrate intakes resulting in the generation of a personal health profile and recommendations and/or instructions comprising: adapting the amount of insulin to be administered, adapting intake of carbohydrates and/or adapting intensity of excercise.

The invention claimed is:

1. A personal health monitoring system, comprising:
an implantable single-chip optical sensor, comprising optical sensing means for continuously sensing biological parameters in bodily fluids of a user, an implantable optical processor for processing sensor data containing data points which are provided by said optical sensing means upon sensing said biological parameters, and a first wireless transceiver for transmitting the processed sensor data, wherein said biological parameters comprise at least a glucose concentration and a ketone bodies concentration in said bodily fluids such that said sensor data comprises at least glucose concentration data points and ketone bodies concentration data points; and
a monitoring device, comprising a display for displaying a personal health profile of the user, a second wireless transceiver for communicating with said first wireless transceiver to receive said processed sensor data,
wherein said implantable optical processor is equipped with an algorithm, which is executable thereon, to:
determine in real-time first trends in said glucose concentration data points and second trends in said ketone bodies concentration data points,
determine in-real time fat and glucose metabolism information based on the glucose concentration data points and the ketone bodies concentration data points,
generate a prediction of ketoacidosis based on the fat and glucose metabolism information,
detect in real-time first user dependent multivariate correlations between information in said first trends and information in said second trends,
generate in real-time the personal health profile of the user based on the first user dependent multivariate correlations, the fat and glucose metabolism information, and includes the prediction of ketoacidosis, and
determine in real-time recommendations or suggestions based on the generated personal health profile,
wherein the monitoring device is configured to communicate in real-time to the user said determined recommendations or suggestions on a user interface of the display when intervention is required, the recommendations or suggestions being aimed at improving the user's health.

2. The personal health monitoring system according to claim 1,
wherein the implantable single-chip optical sensor comprises the implantable optical processor equipped with the algorithm which is executable thereon and which is provided for processing the sensor data before transmitting to the monitoring device, wherein processing the sensor data includes converting the sensor data.

3. The personal health monitoring system according to claim 1, wherein the implantable single-chip optical sensor is a subcutaneous implantable single-chip optical sensor and the bodily fluid is interstitial fluid.

4. The personal health monitoring system according to claim 1, further comprising one or more further implantable single-chip optical sensors.

5. The personal health monitoring system according to claim 1, wherein the algorithm is further configured for:
    determining in real-time third trends in heart rate data points from a heart rate sensor, and
the monitoring device is configured to receive the heart rate data points from the implantable single-chip optical sensor.

6. The personal health monitoring system according to claim 5, wherein said algorithm is further provided for:
    detecting in real-time second user dependent multivariate correlations between information in said third trends and information in said first trends and/or information in said second trends, and
    evaluating in real-time said second user dependent multivariate correlations upon generating said personal health profile.

7. The personal health monitoring system according to claim 5, wherein the implantable single-chip optical sensor comprises the heart rate sensor.

8. The personal health monitoring system according to claim 1, wherein the biological parameters sensed by the optical sensing means of the implantable single-chip optical sensor further comprise at least one of the following: body temperature, urea, lactate, pH, fructosamine, oxaloacetate, oxaloacetate and/or hydration level; such that said sensor data comprises further data points relating to body temperature, urea, lactate, pH, fructosamine, oxaloacetate and/or hydration level; and wherein said algorithm is further provided for:
    determining fourth trends in said further data points.

9. The personal health monitoring system according to claim 8, wherein said algorithm is further provided for:
    determining in real-time the fourth trends in said further data points,
    detecting in real-time third user dependent multivariate correlations between information in said fourth trends and information in said first trends, and/or information in said second trends and/or information in said third trends, and
    evaluating in real-time said third user dependent multivariate correlations upon generating said personal health profile.

10. The personal health monitoring system according to claim 1, further comprising an insulin pump, wherein the personal health profile comprises instructions for a controller of said insulin pump.

11. The personal health monitoring system according to claim 1, wherein the implantable single-chip optical sensor is capable of sensing the biological parameters by using optical means.

12. The personal health monitoring system according to claim 1, wherein a mobile terminal is provided for collecting metadata including at least one of: gender, age, BMI, location data, calories intake data, activity data, agenda information, information on periods, method of anticonception, pregnancy, stress level and/or user habit information, and wherein the algorithm is provided for evaluating said metadata upon generating said personal health profile.

13. The personal health monitoring system according to claim 1, wherein the implantable single-chip optical sensor comprises an integrated controller which is provided for controlling the optical sensing means at a variable sampling rate.

14. The personal health monitoring system according to claim 13, wherein the integrated controller is provided for detecting a variability level in said sensor data and adapting said variable sampling rate according to said detected variability level.

15. The personal health monitoring system according to claim 1, wherein the implantable single-chip optical sensor comprises an integrated memory for accumulating the sensor data and/or components for wireless energy transfer.

16. A method to generate a personal health profile comprising:
   a) measuring glucose concentration data points and ketone bodies concentration data points using an optical sensing means of an implantable single-chip optical sensor,
   b) determining in real-time, by an implantable optical processor in the implantable single-chip optical sensor, first trends in said glucose concentration data points and second trends in said ketone bodies concentration data points,
   c) determine in-real time a fat and glucose metabolism information based on the glucose concentration data points and the ketone bodies concentration data points,
   d) generate a prediction of ketoacidosis based on the fat and glucose metabolism information,
   e) detecting in real-time, by the implantable optical processor, user dependent multivariate correlations between information in said first trends and information in said second trends,
   f) generating in real-time, by the implantable optical processor, the personal health profile of the user based on said user dependent multivariate correlations, the fat and glucose metabolism information, and includes the prediction of ketoacidosis,
   g) determining in real-time, by the processor, recommendations or suggestions based on the generated personal health profile,
   h) transmitting, by a transceiver in the implantable single-chip optical sensor, said determined recommendations or suggestions to a monitoring device, and
communicating in real-time to the user said determined recommendations or suggestions on a user interface of a display in the monitoring device when intervention is required, the recommendations or suggestions being aimed at improving the user's health.

\* \* \* \* \*